(12) United States Patent
Lai et al.

(10) Patent No.: US 8,048,850 B2
(45) Date of Patent: Nov. 1, 2011

(54) COVALENT CONJUGATES BETWEEN ARTEMISININ-RELATED ENDOPEROXIDES AND IRON-CARRYING PROTEINS AND METHODS OF USE

(75) Inventors: Henry C. Lai, Seattle, WA (US); Tomikazu Sasaki, Bothell, WA (US); Narendra P. Singh, Lynnwood, WA (US)

(73) Assignee: University of Washington, Seattle, WA (US)

( * ) Notice: Subject to any disclaimer, the term of this patent is extended or adjusted under 35 U.S.C. 154(b) by 1041 days.

(21) Appl. No.: 10/457,078

(22) Filed: Jun. 6, 2003

(65) Prior Publication Data

US 2004/0067875 A1 Apr. 8, 2004

Related U.S. Application Data

(60) Provisional application No. 60/386,928, filed on Jun. 6, 2002.

(51) Int. Cl.
| | | |
|---|---|---|
| *A61K 38/00* | (2006.01) | |
| *A61K 47/00* | (2006.01) | |
| *A61K 43/00* | (2006.01) | |
| *A61K 35/00* | (2006.01) | |
| *C07D 323/00* | (2006.01) | |
| *A01N 43/02* | (2006.01) | |

(52) U.S. Cl. .......... 514/1.3; 514/1.1; 514/5.4; 514/18.9; 514/19.2; 514/19.3; 549/349; 530/300; 424/1.69

(58) Field of Classification Search ........................ 514/6
See application file for complete search history.

(56) References Cited

U.S. PATENT DOCUMENTS

| | | | |
|---|---|---|---|
| 4,698,387 A | 10/1987 | Schmidt | |
| 5,216,175 A | 6/1993 | Avery et al. | |
| 5,578,637 A * | 11/1996 | Lai et al. ...................... | 514/450 |
| 6,054,133 A * | 4/2000 | Horwitz et al. ............ | 424/248.1 |
| 6,127,405 A | 10/2000 | Kumar | |
| 6,160,004 A | 12/2000 | Posner | |
| 6,214,864 B1 | 4/2001 | Jain et al. | |
| 6,297,272 B1 | 10/2001 | Posner et al. | |
| 6,307,068 B1 | 10/2001 | Li | |
| 6,486,199 B1 | 11/2002 | Vennerstrom et al. | |
| 6,906,205 B2 | 6/2005 | Vennerstrom et al. | |
| 7,692,030 B2 * | 4/2010 | Sasaki et al. .................. | 549/349 |
| 2003/0108556 A1* | 6/2003 | Mekalanos et al. ........ | 424/184.1 |
| 2005/0256185 A1 | 11/2005 | Vennerstrom et al. | |

FOREIGN PATENT DOCUMENTS

| | | |
|---|---|---|
| WO | 85/00812 A1 | 2/1985 |
| WO | 96/34602 A1 | 11/1996 |
| WO | 97/01548 A1 | 1/1997 |
| WO | 00/42046 A1 | 7/2000 |
| WO | 01/04123 A2 | 1/2001 |
| WO | 02/091992 A2 | 11/2002 |

OTHER PUBLICATIONS

Payne. Exploiting intracellular iron and iron-rich compounds to effect tumor cell lysis. (Medical Hypothesis; vol. 61, Issue 2, Aug. 2003, pp. 206-209. (Copy not included as not prior art, but available via PubMed].*

Cornelissen, C.N., "Transferrin-Iron Uptake by Gram-Negative Bacteria," *Frontiers in Bioscience* 8:d836-847, May 1, 2003.

Cumming, J.N., et al., "Design, Synthesis, Derivatization, and Structure-Activity Relationships of Simplified, Tricyclic, 1,2,4-Trioxane Alcohol Analogues of the Antimalarial Artemisinin," *J. Med. Chem.* 41:952-964, 1998.

Efferth, T., et al., "The Anti-Malarial Artesunate Is Also Active Against Cancer," *International Journal of Oncology* 18:767-773, 2001.

Efferth, T., et al., "mRNA Expression Profiles for the Response of Human Tumor Cell Lines to the Antimalarial Drugs Artesunate, Arteether, and Artemether," *Biochemical Pharmacology* 64:617-623, 2002.

Efferth, T., et al., "Activity of Drugs From Traditional Chinese Medicine Toward Sensitive and MDR1- or MRP1-Overexpressing Multidrug-Resistant Human CCRF-CEM Leukemia Cells," *Blood Cells, Molecules, and Diseases* 28(2):160-168, Mar./Apr. 2002.

Evans, R. W., and J.S. Oakhill, "Transferrin-Mediated Iron Acquisition by Pathogenic *Neisseria*," *Biochem. Soc. Trans.* 30(4):705-707, Aug. 2002.

Gray-Owen, S.D., and A.B. Schryvers, "Bacterial Transferrin and Lactoferrin Receptors," *Trends in Microbiology* 4(5):185-191, May 1996.

Lai, H., and N.P. Singh, "Selective Cancer Cell Cytotoxicity From Exposure to Dihydroartemisinin and Holotransferrin," *Cancer Letters* 91:41-46, 1995.

Li, Y., et al., "Novel Antitumor Artemisinin Derivatives Targeting G1 Phase of the Cell Cycle," *Bioorganic & Medicinal Chemistry Letters* 11:5-8, 2001.

Moore, J.C., et al., "Oral Administration of Dihydroartemisinin and Ferrous Sulfate Retarded Implanted Fibrosarcoma Growth in the Rat," *Cancer Letters* 98:83-87, 1995.

Sadava, D., et al., "Transferrin Overcomes Drug Resistance to Artemisinin in Human Small-Cell Lung Carcinoma Cells," *Cancer Letters* 179:151-156, 2002.

Sing, N.P., and H. Lai, "Selective Toxicity of Dihydroartemisinin and Holotransferrin Toward Human Breast Cancer Cells," *Life Sciences* 70:49-56, 2001.

Singh, N.P., and K.B. Verma, "Case Report of a Laryngeal Squamous Cell Carcinoma Treated With Artesunate," *Archive of Oncology* 10(4):249-280, 2002.

Wandersman, C., and I. Stojiljkovic, "Bacterial Heme Sources: the Role of Heme, Hemoprotein Receptors and Hemophores," *Curr. Opin. Microbiol.* 3(2):215-220, Apr. 2000.

Anfosso, L., et al., "Microarray Expression Profiles of Angiogenesis-Related Genes Predict Tumor Cell Response to Artemisinins," *The Pharmacogenomics Journal*, 2006, pp. 1-10.

(Continued)

*Primary Examiner* — Maury Audet

(74) *Attorney, Agent, or Firm* — Christensen O'Connor Johnson Kindness PLLC

(57) ABSTRACT

In one aspect, the invention provides covalent conjugates between artemisinin-related endoperoxides and iron-carrying proteins. In some embodiments, the covalent conjugates comprise artelinate and holotransferrin. In another aspect, the invention provides methods for administering the covalent conjugates of the invention to treat cancer and infections by pathogens that bind iron-carrying proteins.

11 Claims, No Drawings

OTHER PUBLICATIONS

Avery, M.A., et al., Simplified Analogues of the Antimalarial Artemisinin: Synthesis of 6,9-Desmethylartemisinin, *J. Org. Chem.* 54:1792-1795, 1989.

Avery, M.A., et al., "Total synthesis of (+)-Artemisinin and (+)-9-Demethylartemisinin," *Tetrahedron Letters* 28:4629-4632, 1987.

Benoit-Vical, F., et al., "In Vitro and In Vivo Potentiation of Artemisinin and Synthetic Endoperoxide Antimalarial Drugs by Metalloporphyrins," *Antimicrobial Agents and Chemotherapy* 44(10):2836-2841, Oct. 2000.

Bez, G., et al., "Recent Developments With 1,2,4-Trioxane-Type Artemisinin Analogues," *Current Organic Chemistry* 7:1231-1255, 2003.

Gu, H.M., et al., "Antimalarial Activities of 25 Derivatives of Artemisinine Against Chloroquine-Resistant *Plasmodium berghei*," *Acta Pharmacol. Sinica* 1(1):48-50, 1980. (Abstract only).

Imakura, Y., et al., "Acid Degradation Products of Qinghaosu and Their Structure-Activity Relationships," *Heterocycles* 31(6):1011-1016, Jun. 1, 1990. (Abstract only).

Imakura, Y., et al., "Synthesis of Desethanoqinghaosu, a Novel Analogue of the Antimalarial Qinghaosu," *J. Chem. Soc. Chem. Comm.*, 1988, pp. 372-374.

Lin, A.J., et al., "Antimalarial Activity of New Water-Soluble Dihydroartemisinin Derivatives. 2. Stereospecificity of the Ether Side Chain," *J. Med. Chem.* 32(6):1249-1252, Jun. 1989. (Abstract only).

Peters, W., et al., "The Chemotherapy of Rodent Malaria. XLIX. The activities of Some Synthetic 1,2,4-Trioxanes Against Chloroquine-Sensitive and Chloroquine-Resistant Parasites. Part 2: Structure-Activity Studies on *cis*-Fused Cyclopenteno-1,2,4-Trioxanes (Fenozans) Against Drug-Sensitive and Drug-Resistant Liens of *Plasmodium berghei* and *P. yoelii* ssp. NS In Vivo," *Ann. Trop. Med. Parasit.* 87(1):9-16, 1993.

Posner, et al., "Extraordinarily Potent Antimalarial Compounds: New, Structurally Simple, Easily Synthesized, Tricyclic 1,2,4-Trioxanes," *J. Med. Chem.* 35:2495-2467, 1992.

Vennerstrom, J.L., and J.W. Eaton, "Oxidants, Oxidant Drugs, and Malaria," *Journal of Medicinal Chemistry* 31(7):1269-1277, Jul. 1988.

Vennerstrom, J.L., et al., "Dispiro-1,2,4,5-Tetraoxanes: A New Class of Antimalarial Peroxides," *Journal of Medicinal Chemistry* 35:3023-3027, 1992.

Vennerstrom, J.L., et al., "Identification of an Antimalarial Synthetic Trioxolane Drug Development Candidate," *Nature* 430:900-904, Aug. 2004.

Zaman, S.S., and R.P. Sharma, "Some Aspects of the Chemistry and Biological Activity of Artemisinin and Related Antimalarials," *Heterocycles* 32:1593-1638, 1991.

Ferreira, J.F.S., and J. Janick, "Immunoquantitative Analysis of Artemisinin From Artemisia Annua Using Polyclonal Antibodies," *Phytochemisty* 41(1):97-104, 1996.

Zheng, G.Q., "Cytotoxic Terpenoids and Flavonoids From Artemisia Annua," *Planta Med.* 60(1):54-57, 1994 (abstract only).

H. Lai, et al., "Targeted Treatment of Cancer With Artemisinin and Artemisinin-Tagged Iron-Carrying Compounds," *Expert Opin. Ther. Targets* 9(5):995-1007, 2005.

Shoeb, H.A., "Antimicrobial Activity of Artemisinin and its Derivatives Against Anaerobic Bacteria," <http://www.ncbi.nlm.nih.gov/entrez/query.fcgi?db=pubmed&cmd=Retrieve&dopt=AbstractPlus&List_uids...> [retrieved Sep. 1, 2006].

Surolia, N., and S. Misquith, "Cell Surface Receptor Directed Targeting of Toxin to Human Malaria Parasite, *Plasmodium falciparum*," FEBS [Federation of European Biochemical Societies] Letters 396(1):57-61, Oct. 28, 1996.

Woerdenbag, H. J., et al., "Cytotoxicity of Artemisinin-Related Endoperoxides to Ehrlich Ascites Tumor Cells," Journal of Natural Products 56(6):849-856, Jun. 1993.

Beekman, A.C., et al., "Stability of Artemisinin in Aqueous Environments: Impact on Its Cytotoxic Action to Ehrlich Ascites Tumour Cells," Journal of Pharmacy and Pharmacology 49(12):1254-1258, Dec. 1997.

* cited by examiner

COVALENT CONJUGATES BETWEEN ARTEMISININ-RELATED ENDOPEROXIDES AND IRON-CARRYING PROTEINS AND METHODS OF USE

CROSS-REFERENCE TO RELATED APPLICATION

This application claims the benefit of U.S. Provisional Application No. 60/386,928, filed Jun. 6, 2002, under 35 U.S.C. §119.

FIELD OF THE INVENTION

The invention relates to covalent conjugates between artemisinin-related endoperoxides and iron-carrying proteins and the use of these conjugates to treat cancer and infections caused by pathogens that bind iron-carrying proteins.

BACKGROUND OF THE INVENTION

Artemisinin is a sesquiterpene lactone isolated from the plant *Artemisia annua* L, extracts of which has been used to treat malaria for at least 1600 years. The artemisinin molecule contains an endoperoxide bridge that reacts with an iron atom to form free radicals. The anti-malarial action of artemisinin is due to its reaction with intra-parasitic heme to generate free radicals, causing cell death. Cancer cells have a significantly higher influx of iron than normal cells. Accordingly, it has been shown that artemisinin and artemisinin analogs are cytotoxic against established tumors and tumor cell lines (see, e.g., Woerdenbag et al. (1993) *J. Nat. Prod.* 56(6):849-56; Lai & Singh (1995) *Cancer Lett.* 91:41-6; Efferth et al. (2001) *Int. J. Oncol.* 18:767-73; Li et al. (2001) *Bioorg. Med. Chem. Lett.* 11:5-8; Singh & Lai (2001) *Life Sci.* 70:49-56; Efferth et al. (2002) *Biochem. Pharmacol.* 64:617-23; Efferth et al. (2002) *Blood Cells, Molecules & Diseases* 28(2):160-8; Sadava et al. (2002) *Cancer Lett.* 179:151-6).

Many analogs of artemisinin and other compounds containing an endoperoxide bridge that are biologically active have been described (see, e.g., U.S. Pat. No. 5,180,840; U.S. Pat. No. 5,216,175; U.S. Pat. No. 5,225,427; Cumming et al. (1998) *J. Med. Chem.* 41(6):952-64; Posner et al. (1999) *J. Med. Chem.* 42:300-4; Li et al. (2001) *Bioorg. Med. Chem. Lett.* 11:5-8; Wu et al. (2001) *Eur. J. Med. Chem.* 36:469-79; Posner et al. (2003) *J. Med Chem* 46:1060-5). Analogs of artemisinin that have been used in the treatment of malaria include dihydroartemisinin, artemether, artesunate, arteether, propylcarbonate dihydroartemisinin and artelinic acid.

Artemisinin is a relatively safe drug with few and minor side effects even at high doses. Oral doses of 70 mg/kg/day for 6 days has been used in humans for malaria treatment. No apparent adverse side effects were observed after treatment of a cancer patient with artesunate (oral dose of 50 mg per day; intramuscular dose of 60 mg/day, for a period of 9 months) (Singh & Verma (2002) *Arch. Oncol.* 10(4):279-80). Artemisinin and artemisinin analogs have also been used in the treatment of skin conditions such as psoriasis, blistering skin diseases, viral warts, mulluscum contagiosum, and hemorrhoids (see, e.g., U.S. Pat. No. 4,978,676; U.S. Pat. No. 5,219,880). Artemisinin and artemisinin analogs have also been used for malaria prophylaxis.

It has been shown that administration of iron salts or the iron-carrying protein holotransferrin increases the susceptibility of cancer cells and implanted tumors to artemisinin and its analogs (Lai & Singh (1995) *Cancer Lett.* 91:41-46; Moore et al. (1995) *Cancer Lett.* 98:83-7; Singh & Lai (2001) *Life Sci.* 70:49-56; Sadava et al. (2002) *Cancer Lett.* 1179: 151-6).

It has also been shown that certain pathogens obtain iron by binding to iron-carrying host proteins. For example, *Neisseria meningitidis*, the causative agent of bacterial meningitis, expresses cell surface receptors for iron-carrying compounds such as transferrin and lactoferrin (Evans & Oakhill (2002) *Biochem. Soc. Trans.* 30(4):705-7). Currently, no vaccine is available for the B strain of *N. meningitidis*, the most prevalent strain in the Western world. Furthermore, it has been shown that *Helicobacter pylori*, the etiologic agent of gastritis, gastric and duodenal ulcers, and adenocarcinoma in humans, obtains iron by binding human lactoferrin (Husson et al. (1993) *Infect. Immun.* 61 (6):2694-7).

There is a need in the art for artemisinin compositions with increased efficacy for the treatment of cancer and disease caused by pathogens that bind iron-carrying host proteins. There is also a need for methods for treating cancer and infections caused by pathogens that obtain iron by internalizing iron-carrying host proteins. The present invention addresses these needs.

SUMMARY OF THE INVENTION

In one aspect, the invention provides new compounds and compositions comprising covalent conjugates between an artemisinin-related endoperoxide and an iron-carrying protein. The artemisinin-related endoperoxide may be linked to the iron-carrying compound by a hydrazide moiety, a hydrazine moiety, or an aminoxy moiety. In some embodiments, the artemisinin-related endoperoxide has the structure:

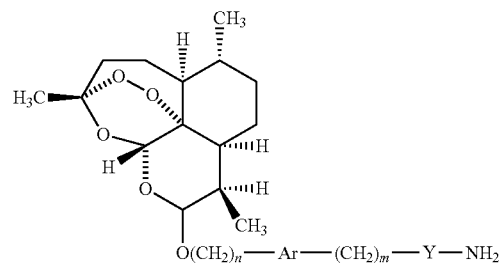

where n=1-3, m=0-3, Ar=aryl, and Y=—(C=O)NH—, —NH—, or —O—. Representative artemisinin-related endoperoxides present in the covalent conjugates of the invention include artelinate and dihydroartemisinin.

Representative iron-carrying proteins present in the covalent conjugates of the invention include the transferrin family of proteins, neutral gelatinase-associated lipocalin (NGAL), hemoproteins, and other iron-binding proteins. Thus, the covalent conjugates may comprise, for example, conjugates of artelinate and holotransferrin, artelinate and hololactoferrin, or artelinate and hemoglobin. The invention also provides compositions comprising the covalent conjugates of the invention and a pharmaceutically acceptable carrier. The covalent conjugates of the invention are useful for treating cancer and infections by pathogens that bind iron-carrying proteins.

In another aspect, the invention provides methods of administering the covalent conjugates of the invention to a subject in need thereof. Exemplary covalent conjugates suitable for administration in this aspect of the invention include, for example, covalent conjugates between artelinate and holotransferrin, between artelinate and hololactoferrin, and between artelinate and hemoglobin.

In some embodiments, the invention provides methods for treating cancer by administering to a human or animal subject in need thereof an effective amount of a composition comprising a covalent conjugate between an artemisinin-related endoperoxide and an iron-carrying protein to a subject in need thereof. The covalent conjugates may be administered topically, systemically, or they may be injected directly into a tumor. The covalent conjugates may be administered alone or in combination with one or more additional therapeutic agents. For example, the covalent conjugates may be administered with an agent that increases the transport of iron into cells, for example by increasing the cell surface number of receptors for the iron-carrying proteins in the conjugate.

The invention also provides methods for treating infections by pathogens that bind to iron-carrying proteins by administering to a human or animal subject in need thereof an effective amount of a composition comprising a covalent conjugate between an artemisinin-related endoperoxide and an iron-carrying protein. In one embodiment, the pathogen comprises *Helicobacter pylori*, wherein the iron-carrying protein comprises human lactoferrin, and wherein the artemisinin-related endoperoxide is selected from the group consisting of artelinate and dihydroartemisinin. In other exemplary embodiments, the pathogen comprises *Neisseria meningitidis*, wherein the iron-carrying protein comprises human transferrin, and wherein the artemisinin-related endoperoxide is selected from the group consisting of artelinate and dihydroartemisinin.

Yet further embodiments provide methods for treating *H. pylori* infections by administering to a human or animal subject in need thereof an effective amount of a composition comprising a covalent conjugate between an artemisinin-related endoperoxide and an iron-carrying protein.

DETAILED DESCRIPTION OF THE PREFERRED EMBODIMENT

In one aspect, the invention provides compositions comprising covalent conjugates between artemisinin-related endoperoxides and iron-carrying proteins. As used herein, the term "covalent conjugate" refers to a compound in which an artemisinin-related endoperoxide is covalently linked to an iron-carrying protein. The term "artemisinin-related endoperoxide" refers to a compound having an endoperoxide bridge, which reacts with an iron atom to form free radicals, causing cell death. Artemisinin-related endoperoxides compounds may also form free radicals in the presence of copper and manganese. Representative artemisinin-related endoperoxides are set forth herein, although it will be apparent that other endoperoxides will be useful for this purpose.

Typically, the artemisinin-related endoperoxide is selected from the group consisting of sesquiterpene lactones and alcohols, carbonates, esters, ethers, and sulfonates thereof, arteflene, 1,2,4-trioxanes, and 1,2,4,5-tetraoxanes. The artemisinin-related endoperoxide may have the structure:

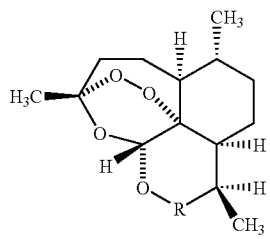

wherein R is

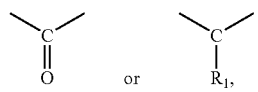

where $R_1$ is hydrogen, hydroxyl, alkyl, or has the formula:

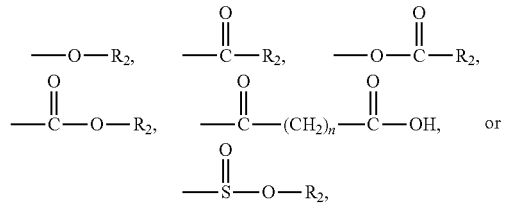

where $R_2$ is alkyl or aryl and n is 1 to 6, and the pharmaceutically acceptable salts thereof. As used herein, the term "alkyl" means lower alkyl having from 1 to 6 carbon atoms, preferably 1 to 4 carbon atoms. Alkyl groups of the invention may be straight-chain or branched-chain groups. The term "aryl" refers to monocyclic and polycyclic aromatic groups containing from 4 to 14 backbone carbon or heteroatoms, and includes both carbocyclic aryl groups and heterocyclic aryl groups. Carbocyclic aryl groups are aryl groups in which all ring atoms are carbon. Heterocyclic aryl groups have from 1 to 4 heteroatoms as ring atoms with the remainder of the ring atoms being carbon. Representative aryl groups include, for example, phenyl and benzyl. Pharmaceutically acceptable salts include the alkali or alkaline earth metal salts, preferably sodium or potassium.

For example, artemisinin-related endoperoxides include artemisinin, where R is

dihydroartemisinin ($R_1$=—OH), artesunic acid ($R_1$=—OCO($CH_2$)$_2CO_2H$), and artesunate, artemether ($R_1$=—OCH$_3$), and arteether ($R_1$=—OC$_2$H$_5$). Other representative endoperoxide compounds of the invention include artelinic acid, dihydroartemisinin propyl carbonate, arteflene (Ro. 42-1611) and its analogs (Biirgen et al. (1994) *Sixth Int. Cong. Infect. Dis. Abst.* 427, p. 152, Prague), 1,2,4-trioxanes (Peters et al. (1993) *Ann. Trop. Med. Parasit.* 87(1):9-16) and 1,2,4,5-tetraoxanes (Vennerstrom et al. (1992) *J. Med. Chem.* 35(16): 3023-3027). Other suitable structural analogs of artemisinin are described in, for example, U.S. Pat. Nos. 5,216,175 and 5,180,840; Cumming et al. (1998) *J. Med. Chem.* 41(6):952-64; and PCT patent applications WO 97/01548, WO 99/33461, and WO 00/42046.

The source of artemisinin-related endoperoxides may be natural (e.g., isolated from plants), synthetic, or semi-synthetic. For example, the free radical-generating agents may be produced by expressing the enzymes for the relevant synthetic pathways in a microbial host (see, e.g., Martin et al. (2003) *Nature Biotechnol.*, published online: Jun. 1, 2003, doi:10.1038/nbt833).

As used herein, the term "iron-carrying protein" refers to a protein that is suitable for transporting iron to or into a cell. The iron-carrying protein in the covalent conjugates of the invention may be a mammalian protein, such as a human protein. Exemplary iron-carrying proteins include the transferrin family of proteins, neutral gelatinase-associated lipocalin (NGAL), hemoproteins, and other iron-binding proteins. Iron plays a vital role in cell growth. The transferrin family of proteins includes transferrin, lactoferrin, ovotransferrin, and melanotransferrin (Aisen & Harris (1989) in *Iron Carriers and Iron Proteins* (ed. Loehr, VCH, New York) pages 273-320; Baker (1994) *Adv. Inorg. Chem.* 41:389-463). All these proteins are structurally related single-chain glycoproteins containing 670-690 amino acids. Transferrin transports iron and heme from the circulation into cells. The iron-loaded form of transferrin (holotransferrin) binds to transferrin receptors on the cell surface and is taken inside the cell via receptor-mediated endocytosis, where the iron is released. Lactoferrin has a key role in iron absorption from human milk. Another function of lactoferrin is to withhold iron from infectious agents. Lactoferrin, unlike transferrin, stably binds iron at low pH and is absorbed into the intestine.

NGAL is an iron-carrying protein that is unrelated to the transferrin family of proteins and is proposed to deliver iron to differentiating epithelial cells (Kaplan (2002) *Cell* 111:603-6). Hemoproteins are proteins such as hemoglobin, myoglobin, hemopexin, cytochromes, catalases, and peroxidases that carry heme as a prosthetic group. For example, hemopexin is a 60 kDa serum glycoprotein that sequesters heme with very high affinity from the blood stream and transports it to the liver (Baker et al. (2003) *Proc. Natl. Acad. Sci. U.S.A.* 100 (7):3579-83).

In the covalent conjugates of the invention, the artemisinin-related endoperoxides are linked to the iron-carrying protein in any way that preserves both the activity of the iron-carrying protein and the activity of the artemisinin-related endoperoxide. For example, the artemisinin-related endoperoxide may be linked to a glycosylated iron-carrying protein by first preparing a hydrazide derivative of the artemisinin-related endoperoxide, which is then linked to one or more oxidized polysaccharide groups on the iron-carrying protein, as described in EXAMPLE 1. To make the hydrazide derivative of the artemisinin-related endoperoxide, an ester of the artemisinin-related endoperoxide may first be formed by adding 1-hydroxybenztriazole (HOBt) to the artemisinin-related endoperoxide, followed by addition of ethyl dimethylethylcarbodiimide. The HOBt ester may then be reacted with hydrazine to form the hydrazide derivative. The hydrazide derivative may then be covalently linked to an iron-carrying protein, in which the polysaccharide groups have been oxidized with an oxidizing agent such as sodium periodate. Any artemisinin-related endoperoxide with a —(C=O)NH— group can be used to make a hydrazide derivative that can be linked to transferrin or other iron-carrying glycoproteins (see, e.g., Cumming et al. (1998) *J. Med. Chem.* 41(6):952-64).

The artemisinin-related endoperoxide may also be linked to a glycosylated iron-carrying protein by first preparing a hydrazine or aminoxy derivative of the artemisinin-related endoperoxide. To make the hydrazine or aminoxy derivative of the artemisinin-related endoperoxide, a halide of the artemisinin-related endoperoxide may first be formed by adding a halo alcohol to the artemisinin-related endoperoxide, followed by addition of boron trifluoride etherate. The halide or the artemisinin-related endoperoxide may then be reacted with hydrazine or hydroxyl amine to form the hydrazine or aminoxy derivative, respectively. The halide group may be substituted by p-toluenesulphonyl or methanesulfonyl group for the reaction. The hydrazine or aminoxy derivative may then be covalently linked to the an iron-carrying protein, in which the polysaccharide groups have been oxidized with an oxidizing agent such as sodium periodate. Any artemisinin-related endoperoxide with a —(C=O)NH— group, a —NH— group, or an —O— group can be used to make either a hydrazine derivative or an aminoxy derivative that can be linked to transferrin or other iron-carrying glycoproteins.

Artemisinin-related endoperoxides that are suitable for linking in this manner include compounds from which a hydrazide, hydrazine, or aminoxy derivative may be prepared without destroying the activity of the endoperoxide bridge. Generally, the hydrazide, hydrazine, or aminoxy group is separated from the endoperoxide bridge by a spacer, such as a hydrocarbon chain. Ethers, esters, amides, sulfides and disulfides may also be used as a spacer. For example, a benzene ring may separate the endoperoxide bridge from the hydrazide, hydrazine, or aminoxy group, as in artelinate. Accordingly, artemisinin-related endoperoxides suitable for use according to the invention include, but are not limited to, endoperoxides of the structure:

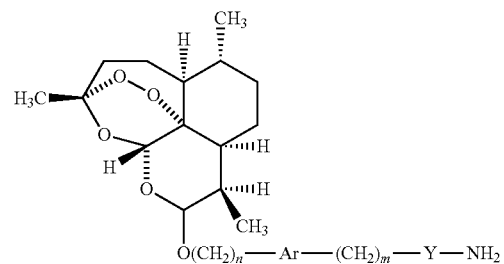

where n=1-3, m=0-3, Ar=aryl, for example, phenyl, naphtyl, pyrenyl, pyridyl, or pyrimidinyl, and Y=—(C=O)NH—, —NH—, or —O—. Representative artemisinin-related endoperoxides present in the covalent conjugates of the invention include artelinate and dihydroartemisinin.

Other methods for linking an artemisinin-related endoperoxide to an iron-carrying glycoprotein include borate-mediated linkages to carbohydrate residues on the iron-carrying glycoprotein (see, e.g., U.S. Pat. No. 5,919,708). Thus, artemisinin-related endoperoxides with a borate group will react with an 1,2-diol moiety of carbohydrate residues on the protein surface.

For non-glycosylated iron-carrying proteins, artemisinin-related endoperoxides may be linked to the protein surface by using amino acid side chains, as described in EXAMPLE 2. For example, both artesunate and artelinate have a free carboxylic acid group that can be activated with N-hydroxy succinimide (see, e.g., Lewis et al. (1994) *Bioconj. Chem.* 5(6):655-76) and a water soluble carbodiimide reagent such as N-etheyl-N'-dimethylaminoethylcarbodiimide to form an active ester. This active ester may be mixed with an aqueous solution of a non-glycosylated iron-carrying protein to link the artemisinin-related endoperoxide to Lys residues on the protein surface.

The covalent conjugates may be purified by using standard methods in the art, for example by using gel-filtration chromatography, ion-exchange, and reverse-phase or hydrophobic interaction High-Pressure Liquid Chromatography (HPLC). The number of molecules of artemisinin-related endoperoxide bound to one molecule of iron-carrying protein may be determined by using standard methods in the art, for example ion-spray mass spectrometry. The ratio of artemisinin-related endoperoxide to iron-carrying proteins in the covalent conjugates will depend on the iron-carrying protein being used and the method of forming the conjugate. For example, covalent conjugates containing between 1 and 10 molecules of the artemisinin-related endoperoxide per molecule of holotransferrin may be obtained using the method described in EXAMPLE 1.

The invention also provides compositions comprising the covalent conjugates of the invention. In some embodiments, the compositions of the invention comprise a covalent conjugate between artelinate and human holotransferrin, as described in EXAMPLE 1. In other embodiments, the compositions comprise a covalent conjugate between artelinate and human hololactoferrin.

The covalent conjugates of the invention are useful for treating cancer. Due to their rapid rate of division, most cancer cells have high rates of iron intake and express higher cell surface concentrations of transferrin receptors than normal cells. It has been shown that administration of iron salts or holotransferrin increases the susceptibility of cancer cells to artemisinin and its analogs (Moore et al. (1995) *Cancer Lett.* 98:83-7; Singh & Lai (2001) *Life Sci.* 70:49-56; Sadava et al. (2002) *Cancer Lett.* 1179:151-6). Thus, the efficacy and selectivity of the artemisinin-related endoperoxides against cancer is increased by covalently linking artemisinin-related endoperoxides to iron-carrying proteins such as holotransferrin because both endoperoxide and iron are transported to or into the same cell at the same time.

The covalent conjugates of the invention are also useful for treating infections by pathogenic organisms that have receptors for the iron-carrying protein in the covalent conjugates. To establish a successful infection, a pathogen must overcome the strict iron limitations imposed by the host. To overcome this limitation, many pathogens obtain iron from iron-carrying host proteins (see, e.g., Cornelissen, (2003) *Front. Biosci.* 8:D836-47). For example, *Neisseria meningitidis*, the causative agent of bacterial meningitis, expresses cell surface receptors for the iron-carrying proteins transferrin and lactoferrin (Evans & Oakhill (2002) *Biochem. Soc. Trans.* 30(4): 705-7), *Helicobacter pylori*, the etiologic agent of gastritis and peptic ulcer disease in humans, expresses a receptor for human lactoferrin (Husson et al. (1993) *Infect. Immun.* 61(6): 2694-7), and *Staphylococcus aureus* expresses receptors for hemoglobin (Mazmanian et al. (2003) *Science* 299:906-9) Thus, the covalent conjugates of the invention are useful for killing pathogenic organisms that have receptors for the iron-carrying protein in the conjugate. For example, a covalent conjugate between an artemisinin-related endoperoxide and human transferrin or human hololactoferrin may be used to treat bacterial meningitis caused by *N. meningitidis* or gastritis and peptic ulcer disease caused by *Helicobacter pylori*.

According to the methods of the invention, the covalent conjugates between an artemisinin-related endoperoxide and an iron-carrying protein possess superior cytotoxic activities when administered to cancer cells compared to separately administering the artemisinin-related endoperoxide and the iron-carrying protein. In addition, the covalent conjugates of the invention are effective at killing pathogens with receptors for iron-carrying proteins.

In a second aspect, the invention provides methods for administering compositions comprising a covalent conjugate between an artemisinin-related endoperoxide and an iron-carrying protein to a subject in need thereof. The covalent conjugates between artemisinin-related endoperoxides and iron-carrying proteins are as described above. For example, some embodiments provide covalent conjugates between artelinate and holotransferrin, as described in EXAMPLE 1.

These methods are applicable to any animal subject, such as a human subject. For example, a subject in need of compositions comprising a covalent conjugate between an artemisinin-related endoperoxides and an iron-carrying protein may be a cancer patient. As described above, rapidly proliferating cells such as cancer cells generally possess higher concentrations of cell surface transferrin receptors. The methods provide a mechanism for selectively delivering both the endoperoxide moiety and the iron it reacts with to rapidly proliferating cells, such as cancer cells. Accordingly, the invention provides methods for treating cancer by administering to a human or animal subject in need thereof an effective amount of a compound comprising a covalent conjugate between an artemisinin-related endoperoxide and an iron-carrying protein. Other conditions in which there is hyperproliferation of cells and which may be treated with the covalent conjugates of the invention include, but are not limited to, restenosis, autoimmune disease, arthritis, graft rejection, inflammatory bowel disease, or proliferation induced after medical procedures. In some embodiments, the methods comprise administering a compound comprising a covalent conjugate between artelinate and human holotransferrin.

The compounds and compositions comprising a covalent conjugate between an artemisinin-related endoperoxide and an iron-carrying protein may also be administered for treating an infection by a pathogen expressing cell-surface receptors for the iron-carrying proteins in the covalent conjugate. As used herein, the term "treating an infection by a pathogen" refers to inhibiting the growth of the pathogen and/or preventing or ameliorating the symptoms of disease associated with the infection.

Exemplary pathogens with receptors for iron-carrying host proteins are described above and include *Neisseria meningitidis*, which expresses a receptor for human transferrin and *H. pylori*, which expresses a receptor for human lactoferrin. *S. aureas* has recently been shown to express a receptor for hemoglobin (Mazmanian et al. (2003) *Science* 299:906-9), and similar proteins are also expressed by *Listeria monocytogenes* and *Bacillus anthracis* (Cabanes et al. (2002) *Trends. Microbiol.* 10(5):238-45). An exemplary list of pathogens that express receptors for iron-carrying host proteins are shown in Table 1. Once the iron-carrying protein is bound to the receptor expressed by pathogen, the iron or heme is generally released from the iron-carrying protein and transported into the cell (see, e.g., Gray-Owens & Schryvers (1996) *Trends Microbiol.* 4(5):185-91; Wandersman & Stojiljkovic (2000) *Curr. Op. Microbiol.* 3:215-20).

TABLE 1

Receptors for Iron-Carrying Proteins in Human and Animal Pathogens

| Pathogen | Host | Disease | Receptor |
| --- | --- | --- | --- |
| *Moraxella bovis* | Bovine | Kerato-conjunctivitis | Transferrin, lactoferrin[1] |
| *Moraxella catarrhalis* | Human | Otitis media | Transferrin, lactoferrin[1] |
| *Moraxella lacunata* | Human | Kerato-conjunctivitis | Transferrin, laetoferrin[1] |
| *Neisseria meningitidis* | Human | Meningitis | Transferrin, lactoferrin, hemoglobin[1,19] |
| *Neisseria gonorrheae* | Human | Gonorrhea | Transferrin, lactoferrin, hemoglobin[1,18] |
| *Actinobacillus actinomycetecomitans* | Human | Juvenile periodontitis | Transferrin[1] |
| *Actinobacillus equuli* | Equine | Septicemia | Transferrin[1] |
| *Actinobacillus pleuropneumoniae* | Porcine | Pneumonia | Transferrin[1] |
| *Haemophilus agnii* | Ovine | Septicemia | Transferrin[1] |
| *Haemophilus avium* | Poultry | Sinusitis | Transferrin[1] |
| *Haemophilus influenzae* | Human | Meningitis, otitis media | Transferrin, hemoglobin[1,20] |
| *Haemophilus paragallinarum* | Poultry | Infectious coryza | Transferrin[1] |
| *Haemophilus somnus* | Bovine | Thromboembolic meningoencephalitis | Transferrin[1] |
| *Haemophilus parasuis* | Porcine | Glasser's disease | Transferrin[1] |
| *Haemophilus ducreyi* | Human | Genital ulcer disease | Hemoglobin[15] |
| *Pasteurella haemolytica* | Bovine, ovine, caprine | Shipping fever, pasteurellosis | Transferrin[1] |
| *Pasteurella multocida* | Bovine | Pneumonia, septicemia | Transferrin[1] |
| *Staphylococcus aureus* | Human | Bacteremia, pneumonia, endocarditis, septic arthritis, osteomyelitis, deep abscesses, food poisoning | Transferrin, hemoglobin[2,13] |
| *Staphylococcus epidermidis* | Human | Endocarditis, endopthalmitis, septicemia, cystitis | Transferrin[2] |
| *Streptococcus pneumoniae* | Human | Pneumonia, meningitis, bacteremia, otitis media | Lactoferrin[3] |
| *Leishmania chagasi* | Human | Leishmaniasis | Transferrin, lactoferrin[4] |
| *Escherichia coli* K88 | Porcine | Enteropathogenesis | Transferrin[5] |
| *Tritrichonomas foetus* | Cattle | Trichomoniasis | Lactoferrin, hemoglobin[6,] |
| *Treponema pallidum* | Human | Syphilis | Lactoferrin[7] |
| *Mycoplasma pneumonia* | Human | Pneumonia | Lactoferrin[8] |
| *Bordetella pertussis* | Human | Whooping cough | Lactoferrin[9] |
| *Trichonomas vaginalis* | Human | Vaginosis | Lactoferrin[10] |
| *Aeromonas salmonicida* | Fish | Furunculosis | Transferrin, lactoferrin[11] |
| *Helicobacter pylori* | Human | Gastritis, gastric and duodenal ulcers, gastric adenocarcinoma, lymphoma | Lactoferrin[12] |
| *Yersinia enterocolitica* | Human | Enteritis | Hemoglobin, myoglobin, hemopexin, catalase, albumin-heme[14] |
| *Vibrio vulnificus* | Eel | Food poisoning, septicemia, wound infections | Hemoglobin[16] |

TABLE 1-continued

Receptors for Iron-Carrying Proteins in Human and Animal Pathogens

| Pathogen | Host | Disease | Receptor |
|---|---|---|---|
| Porphyromonas gingivalis | Human | Periodontal disease | Hemoglobin[17] |

[1]Gray-Owen & Schryvers (1996) Trends Microbiol. 4(5): 185-91
[2]Modun et al. (1998) Infect. Immun. 66(8): 3591-6
[3]Hammerschmidt et al. (1999) Infect. Immun. 67(4): 1683-7
[4]Britigan et al. (1998) Adv. Exp. Med. Biol. 443: 135-40
[5]Grange et al. (1997) Adv. Exp. Med. Biol. 412: 357-61
[6]Tachezy et al. (1996) Exp. Parasitol. 83(2): 216-28
[7]Alderete et al. (1988) Genitourin. Med. 64(6): 359-63
[8]Tryon & Baseman (1987) Microb. Pathog. 3(6): 437-43
[9]Redhead et al. (1987) J. Gen. Microbiol. 133(4): 891-8
[10]Peterson & Alderete (1984) J. Exp. Med. 160(2): 398-410
[11]Chart & Trust (1983) J. Bacteriol. 156(2): 758-64
[12]Dhaenens et al. (1997) Infect. Immun. 65(2): 514-8
[13]Mazmanian et al. (2003) Science 299: 906-9
[14]Bracken et al. (1999) J. Bacteriol. 181(19): 6063-72
[15]Al-Twafiq et al. (2000) J. Infect. Dis. 181(3): 1049-54
[16]Fouz et al. (1997) Microbiol. Lett. 156(2): 187-91
[17]Simpson et al. (2000) J. Bacteriol. 182(10): 5737-48
[18]Chen et al. (1996) Infect. Immun. 64: 5008-14
[19]Stojiljkovic et al. (1996) J. Bacteriol. 179(15): 4670-78
[20]Frangipane et al. (1994) FEMS Microbiol. Lett. 118: 243-8

The methods of this aspect of the invention provide a mechanism for selectively delivering an endoperoxide moiety and the iron it reacts with directly to the cell membrane of a pathogenic organisms by binding of the covalent conjugate to a receptor for iron-carrying protein. According to the methods of the invention, the endoperoxide moiety in the bound covalent conjugate reacts with the iron or heme released from the iron-carrying protein, producing harmful free radicals in close proximity to the pathogen. Accordingly, the invention provides methods for treating disease caused by *Helicobacter pylori* by administering an effective amount of a composition comprising a covalent conjugate between an artemisinin-related endoperoxide and human hololactoferrin to a human subject in need thereof. The invention also provides methods for treating disease caused by *Neisseria meningitidis* by administering an effective amount of a composition comprising a covalent conjugate between an artemisinin-related endoperoxide and human holotransferrin to a human subject in need thereof.

Other exemplary infections that may be treated by administering an effective amount of a composition comprising a covalent conjugate of the invention include topical bacterial infections, such as gingivitis, skin, and eye infections.

Effective amounts of the covalent conjugates will generally range up to the maximally tolerated dosage, but the concentrations are not critical and may vary widely. The precise amounts employed by the attending physician will vary, of course, depending on the compound, route of administration, physical condition of the patient and other factors. The daily dosage may be administered as a single dosage or may be divided into multiple doses for administration.

The amount of the conjugates of the invention actually administered will be a therapeutically effective amount, which term is used herein to denote the amount needed to produce a substantial beneficial effect. Effective doses may be extrapolated from dose-response curves derived from in vitro or animal model test systems. The animal model is also typically used to determine a desirable dosage range and route of administration. Such information can then be used to determine useful doses and routes for administration in humans or other mammals. The determination of an effective dose is well within the capability of those skilled in the art.

Thus, the amount actually administered will be dependent upon the individual to which treatment is to be applied, and will preferably be an optimized amount such that the desired effect is achieved without significant side-effects.

Therapeutic efficacy and possible toxicity of the covalent conjugates of the invention may be determined by standard pharmaceutical procedures, in cell cultures or experimental animals (e.g., $ED_{50}$, the dose therapeutically effective in 50% of the population; and $LD_{50}$, the dose lethal to 50% of the population). The dose ratio between therapeutic and toxic effects is the therapeutic index, and it can be expressed as the ratio $LD_{50}$ to $ED_{50}$. Covalent conjugates that exhibit large therapeutic indices are particularly suitable in the practice of the methods of the invention. The data obtained from cell culture assays and animal studies may be used in formulating a range of dosage for use in humans or other mammals. The dosage of such conjugates lies preferably within a range of circulating concentrations that include the $ED_{50}$ with little or no toxicity. The dosage typically varies within this range depending upon the dosage form employed, sensitivity of the patient, and the route of administration. Thus, optimal amounts will vary with the method of administration, and will generally be in accordance with the amounts of conventional medicaments administered in the same or a similar form.

The covalent conjugates of the invention may be administered alone, or in combination with one or more additional therapeutically active agents. For example, in the treatment of cancer, the conjugates may be administered in combination with therapeutic agents including, but not limited to, androgen inhibitors, such as flutamide and luprolide; antiestrogens, such as tomoxifen; antimetabolites and cytotoxic agents, such as daunorubicin, fluorouracil, floxuridine, interferon alpha, methotrexate, plicamycin, mecaptopurine, thioguanine, adriamycin, carmustine, lomustine, cytarabine, cyclophosphamide, doxorubicin, estramustine, altretamine, hydroxyurea, ifosfamide, procarbazine, mutamycin, busulfan, mitoxantrone, carboplatin, cisplatin, streptozocin, bleomycin, dactinomycin, and idamycin; hormones, such as medroxyprogesterone, estramustine, ethinyl estradiol, estradiol, leuprolide, megestrol, octreotide, diethylstilbestrol, chlorotrianisene, etoposide, podophyllotoxin, and goserelin; nitrogen mustard derivatives, such as melphalan, chlorambucil, methlorethamine, and thiotepa, steroids, such as betamethasone; and other antineoplastic agents, such as live *Mycobacterium bovis*, dicarbazine, asparaginase, leucovorin, mitotane, vincristine, vinblastine, and taxotere. Appropriate amounts in each case will vary with the particular agent, and will be either readily known to those skilled in the art or readily determinable by routine experimentation.

The covalent conjugates of the invention may also be administered in combination with an agent that increases iron transport into cells, for example, by increasing the cell surface number of receptors for the iron-carrying protein in the conjugate. It has been shown for example, that insulin, insulin-like growth factor I, and epidermal growth factor cause an increase in the number of transferrin receptors at the cells surface (see, e.g., Davis et al. (1987) *J. Biol. Chem.* 261(19): 8708-11; Davis et al. (1986) *J. Biol. Chem.* 262(17):13126-34). Therefore, in some embodiments, covalent conjugates of the invention containing transferrin are administered in combination with insulin, insulin-like growth factor I, or epidermal growth factor.

Administration of the covalent conjugates of the invention is accomplished by any effective route, e.g., parenterally or orally. Methods of administration include topical (for examples, skin patches), inhalational, buccal, intraarterial, subcutaneous, intramedullary, intravenous, intranasal, intrarectal, intraocular administration, and other conventional means. For example, the covalent conjugates may be injected directly into a tumor, into the vicinity of a tumor, or into a blood vessel that supplies blood to the tumor.

The covalent conjugates of the invention may be formulated into a composition that additionally comprises suitable pharmaceutically acceptable carriers, including excipients and other compounds that facilitate administration of the covalent conjugate to a mammalian subject. Further details on techniques for formulation and administration may be found in the latest edition of "Remington's Pharmaceutical Sciences" (Maack Publishing Co, Easton Pa.).

Compositions for oral administration may be formulated using pharmaceutically acceptable carriers well known in the art, in dosages suitable for oral administration. Such carriers enable the compositions containing covalent conjugates of the invention to be formulated as tablets, pills, dragees, capsules, liquids, gels, syrups, slurries, suspensions, etc., suitable for ingestion by a subject. Compositions for oral use may be formulated, for example, in combination with a solid excipient, optionally grinding the resulting mixture, and processing the mixture of granules, after adding suitable additional compounds, if desired, to obtain tablets or dragee cores. Suitable excipients include carbohydrate or protein fillers. These include, but are not limited to, sugars, including lactose, sucrose, mannitol, or sorbitol, starch from corn, wheat, rice, potato, or other plants; cellulose such as methyl cellulose, hydroxypropylmethyl-cellulose, or sodium carboxymethyl-cellulose; and gums including arabic and tragacanth; as well as proteins, such as gelatin and collagen. If desired, disintegrating or solubilising agents may be added, such as the cross-linked polyvinyl pyrrolidone, agar, alginic acid, or a salt thereof, such as sodium alginate.

Dragee cores are provided with suitable coatings such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound (i.e., dosage).

Covalent conjugates for oral administration may be formulated, for example, as push-fit capsules made of gelatin, as well as soft, sealed capsules made of gelatin and a coating such as glycerol or sorbitol. Push-fit capsules may contain covalent conjugates mixed with filler or binders such as lactose or starches, lubricants such as talc or magnesium stearate, and, optionally, stabilizers. In soft capsules, the covalent conjugates may be dissolved or suspended in suitable liquids, such as fatty oils, liquid paraffin, or liquid polyethylene glycol with or without stabilizers.

Compositions for parenteral administration include aqueous solutions of one or more covalent conjugates of the invention. For injection, the covalent conjugates may be formulated in aqueous solutions, such as in physiologically compatible buffers such as Hank's solution, Ringer's solution, or physiologically buffered saline. Aqueous injection suspensions may contain substances, which increase the viscosity of the suspension, such as sodium carboxymethyl cellulose, sorbitol, or dextran. Additionally, suspensions of the covalent conjugates may be prepared as appropriate oily injection suspensions. Suitable lipophilic solvents or vehicles include fatty oils such as sesame oil, or synthetic fatty acid esters, such as ethyl oleate or triglycerides, or liposomes. Optionally, the suspension may also contain suitable stabilizers or agents, which increase the solubility of the covalent conjugate to allow for the preparation of highly concentrated solutions.

For topical or nasal administration, penetrants appropriate to the particular barrier to be permeated are typically used in the formulation. Examples of these are 2-pyrrolidone, N-methyl-2-pyrrolidone, dimethylacetamide, dimethyl-formamide, propylene glycol, methyl or isopropyl alcohol, dimethyl sulfoxide, and azone. Additional agents may further be included to make the formulation cosmetically acceptable. Examples of these are fats, waxes, oils, dyes, fragrances, preservatives, stabilizers, and surface-active agents. Keratolytic agents such as those known in the art may also be included. Examples are salicylic acid and sulfur. For topical administration, the composition may be in the form of a transdermal ointment or patch for systemic delivery of the compound and may be prepared in a conventional manner (see, e.g., Barry, Dermatological Formulations (Drugs and the Pharmaceutical Sciences—Dekker); Harrys Cosmeticology (Leonard Hill Books).

For rectal administration, the compositions may be administered in the form of suppositories or retention enemas. Such compositions may be prepared by mixing the covalent conjugates with a suitable non-irritating excipient that is solid at ordinary temperatures but liquid at the rectal temperature and will therefore melt in the rectum to release the drug. Suitable excipients include, but are not limited to, cocoa butter and polyethylene glycols.

The amounts of each of these various types of additives will be readily apparent to those skilled in the art, optimal amounts being the same as in other, known formulations designed for the same type of administration. Stratum corneum penetration enhancers, for example, will typically be included at levels within the range of about 0.1% to about 15%.

Compositions containing the covalent conjugates of the present invention may be manufactured in a manner similar to that known in the art (e.g., by means of conventional mixing, dissolving, granulating, dragee-making, levigating, emulsifying, encapsulating, entrapping or lyophilizing processes). The compositions may also be modified to provide appropriate release characteristics, e.g., sustained release or targeted release, by conventional means (e.g., coating).

Compositions containing the covalent conjugates may be provided as a salt and can be formed with many acids, including but not limited to hydrochloric, sulfuric, acetic, lactic, tartaric, malic, succinic, etc. Salts tend to be more soluble in aqueous or other protonic solvents than are the corresponding free base forms.

After compositions formulated to contain covalent conjugates and an acceptable carrier have been prepared, they can be placed in an appropriate container and labeled for use.

The following examples merely illustrate the best mode now contemplated for practicing the invention, but should not be construed to limit the invention.

EXAMPLE 1

This Example describes a method for making a representative composition of the invention containing one or more artemisinin-related endoperoxide molecules covalently linked to a molecule of holotransferrin.

Synthesis of Artelinic Acid Hydrazide (ART-NH—$NH_2$): Attempts to prepare an hydrazide derivative of artesunate were unsuccessful and resulted in the formation of dihydroartemisinin due to the cyclization reaction. Artelinate was synthesized from dihydroartemisinin as previously described (Shrimali et al. (1998) *Indian J. Chem.* 37B:1161-1163). Artelinic acid (0.1 g, 0.24 mmol) was dissolved in anhydrous acetonitrile (0.48 mL). To this solution, 1-hydroxybenztriazole (HOBt) (0.038 g, 0.29 mmol) was added, followed by addition of ethyl dimethylethylcarbodiimide (0.055 g, 0.29 mmol). The reaction mixture was stirred at room temperature and monitored by thin-layer chromatography (TLC) until all the acid was converted to the HOBt ester.

A solution of hydrazine (0.46 mL, 0.48 mmol) in acetonitrile (0.48 mL) was cooled to 0° C., and the above reaction mixture was added to it while maintaining the temperature between 0-10° C. The reaction was complete in 10 minutes, as measured by TLC. The reaction mixture was poured into water (5 mL), extracted with ethylacetate (3×10 mL), and washed with brine. The organic phase was separated, dried over anhydrous sodium sulfate, and evaporated to dryness. The crude product was purified by silica gel chromatography using a gradient of methanol/chloroform to give the pure product (0.078 g) in 76% yield.

Synthesis of Artelinate-Holotransferrin Conjugate: Holotransferrin (2 mg), dissolved in 1 ml of 0.1 mol/L sodium acetate pH 5.5, was oxidized at a level of its glycans, at room temperature for 30 minutes with 10 mmol/L sodium periodate. The solution was applied to a short Sephadex G-25 column equipped with a UV monitor. The column was eluted with 0.1 mol/L sodium acetate pH 5.5, and the protein fractions were collected. A solution of excess ART-NH—NH2 was added to the oxidized holotransferrin, and the reaction was kept overnight at room temperature with gentle shaking. The artelinate-holotransferrin conjugate solution was then applied to a Sephadex G-25 column to remove excess ART-NH—NH2. The column was eluted with 0.1 mol/L Tris-HCl buffer, pH 7.5 and the protein fractions were collected. The conjugate was stored at 4° C.

The artelinate-holotransferrin conjugate was purified by hydrophobic interaction HPLC to obtain a homogenous protein conjugate. The number of artelinate molecules per molecule of holotransferrin was determined by ion-spray mass spectrometry.

While the preferred embodiment of the invention has been illustrated and described, it will be appreciated that various changes can be made therein without departing from the spirit and scope of the invention.

EXAMPLE 2

This Example describes a method for making a representative composition of the invention containing one or more artemisinin-related endoperoxide molecules covalently linked to a molecule of hemoglobin.

For covalent modification of non-glycosylated proteins such as hemoglobin with artemisinin derivatives, carboxylic acid derivatives of artemisinin such as artelinic acid is first activated as an N-hydroxy succinimide (HOSu) ester to react with lysine residues on the protein surface. Artelinic acid (4.2 mg, 0.01 mmol) is dissolved in dimethylformamide (DMF) (0.5 mL), and the solution is cooled in ice-bath. To this solution, N-ethyl-N'-dimethlyaminoethyl carbodiimide (EDC) (1.5 mg, 0.01 mmol) and HOSu (1.1 mg, 0.01 mmol) are added. The reaction mixture is kept stirring for 2 hours at 0° C. to complete the formation of the HOSu ester of artelinic acid.

Hemoglobin (10 mg) is dissolved in 0.1 M phosphate buffer 7.0 (5 mL). The DMF solution of the artelinic acid HOSu ester is slowly added with stirring at 0° C. to the solution of hemoglobin. The reaction mixture is kept stirring for 2 hours at 0° C., and for another 2 hours at room temperature. The reaction mixture is then applied to the Sephadex G-25 column which is equilibrated with 0.1 M phosphate buffer pH 7, and the column is eluted with the same buffer. The modified hemoglobin elutes at the void volume. The fractions containing hemoglobin are combined, and then purified by hydrophobic interaction HPLC. The number of artemisinin derivatives attached to the protein is determined by ion spray mass spectrometry.

The embodiments of the invention in which an exclusive property or privilege is claimed are defined as follows:

1. A conjugate comprising:
a protein selected from the group consisting of transferrin, holotransferrin, lactoferrin, and hololactoferrin having covalently coupled thereto one or more endoperoxides having the structure wherein R is C=O; CH—$R_1$, where $R_1$ is (a) hydroxyl, (b) —O—C(O)—$(CH_2)_n$—COOH where n is 1 to 6, or (c) —O—$(CH_2)_n$—Ar—$(CH_2)_m$—Y—$NH_2$ where n=1-3, m=0-3, Ar=aryl, and Y=—(C=O)NH—, —NH—, or —O—; or pharmaceutically acceptable salts thereof;

wherein the one or more endoperoxides are covalently coupled through R to one or more polysaccharide groups on the protein through a linker comprising a hydrazide moiety, a hydrazine moiety, an aminoxy moiety, or a borate moiety.

2. The conjugate of claim 1, wherein the one or more endoperoxides are artelinate.

3. The conjugate of claim 1, wherein the one or more endoperoxides have the structure:

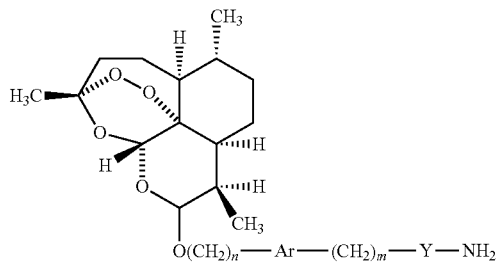

O(CH$_2$)$_n$—Ar—(CH$_2$)$_m$—Y—NH$_2$ where n=1-3, m=0-3, Ar=aryl, and Y=—(C=O)NH—, —NH—, or —O—.

4. The conjugate of claim 1, wherein the protein is holotransferrin.

5. The conjugate of claim 1, wherein the protein is hololactoferrin.

6. The conjugate of claim 1, wherein the one or more endoperoxides are artelinate and the protein is holotransferrin.

7. The conjugate of claim 1, wherein the one or more endoperoxides are artelinate and the protein is hololactoferrin.

8. The conjugate of claim 1, wherein the one or more endoperoxides are artemisinin, dihydroartemisinin, artelinate, artesunic acid, artesunate, or artelinic acid.

9. The conjugate of claim 1, wherein between 1 and 10 endoperoxides are covalently coupled to the one or more polysaccharide groups on the protein.

10. A composition, comprising a pharmaceutically acceptable carrier and the conjugate of claim 1.

11. The composition of claim 10, wherein the one or more endoperoxides are artemisinin, dihydroartemisinin, artelinate, artesunic acid, artesunate, or artelinic acid.

* * * * *